United States Patent [19]

Kroushl et al.

[11] 4,411,869
[45] Oct. 25, 1983

[54] MULTIPLE STAGE REACTOR SYSTEM

[75] Inventors: Joseph A. Kroushl, Westchester; Arthur R. Greenwood, Niles, both of Ill.

[73] Assignee: UOP Inc., Des Plaines, Ill.

[21] Appl. No.: 470,428

[22] Filed: Feb. 28, 1983

Related U.S. Application Data

[63] Continuation-in-part of Ser. No. 334,502, Dec. 28, 1981.

[51] Int. Cl.³ .................................................. B01J 8/12
[52] U.S. Cl. .................................. 422/188; 208/169; 422/197; 422/216; 422/218
[58] Field of Search ............... 422/188, 216, 218, 220, 422/191–197, 236–239, 141, 145; 48/214 A; 208/138, 169; 55/474, 479; 203/29, 41; 201/34; 202/262

[56] References Cited

U.S. PATENT DOCUMENTS

| | | | |
|---|---|---|---|
| 1,982,099 | 11/1934 | Hechenbleikner | 55/474 |
| 2,617,718 | 11/1952 | Miller | 422/218 |
| 2,683,654 | 7/1954 | Bergman | 422/218 |
| 3,692,496 | 9/1972 | Greenwood et al. | 422/191 |
| 3,706,536 | 12/1972 | Greenwood et al. | 422/193 X |
| 3,725,248 | 4/1973 | Greenwood et al. | 208/138 |
| 3,882,015 | 5/1975 | Carson | 208/169 |
| 3,918,930 | 11/1975 | Forbes et al. | 208/169 X |
| 4,040,794 | 8/1977 | Stone | 208/169 X |

Primary Examiner—Richard L. Chiesa
Attorney, Agent, or Firm—James R. Hoatson, Jr.; John F. Spears, Jr.; William H. Page, II

[57] ABSTRACT

The reactor system of this invention comprises two or more vertically spaced or stacked reaction chambers each of which contains two or more vertically positioned annular-form catalyst-retaining sections existing side-by-side, each of said catalyst-retaining sections being defined by an inner tubular-form catalyst-retaining screen coaxially disposed within a vertically positioned outer tubular-form catalyst-retaining screen. Catalyst particles are movable through the resulting annular-form catalyst sections in a dense phase via gravity flow. A reactant stream is processed serially through said reaction chambers, and contacted with catalyst within said annular-form catalyst-retaining sections in a manner to promote uniform flow of reactants across said sections. The disclosed reactor system is of particular advantage with respect to a relatively low pressure hydrocarbon conversion process.

20 Claims, 2 Drawing Figures

U.S. Patent  Oct. 25, 1983  4,411,869
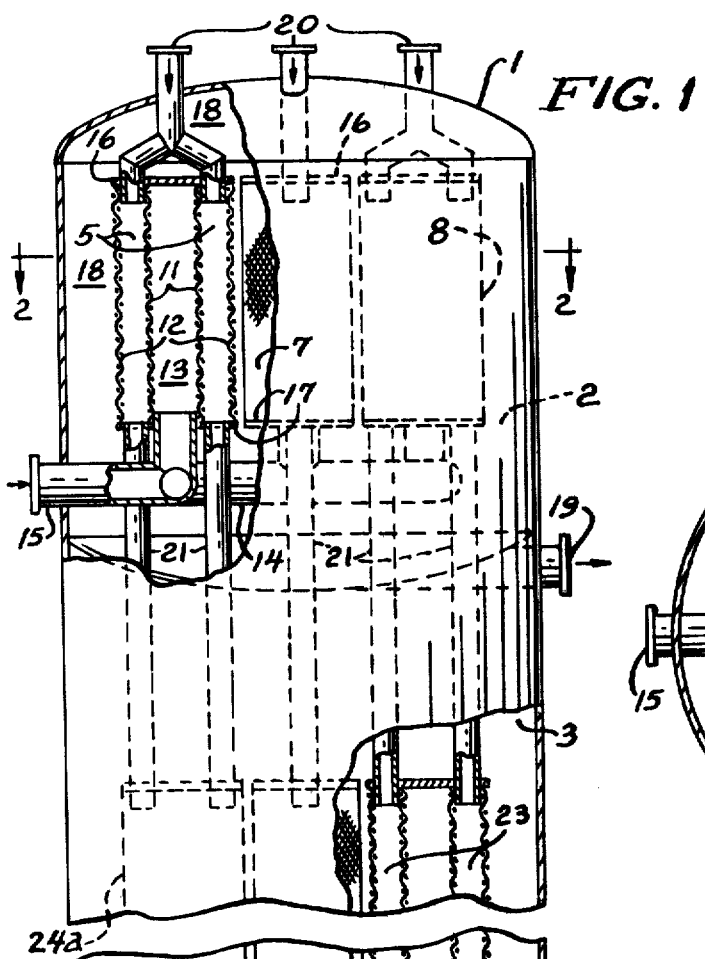
FIG. 1
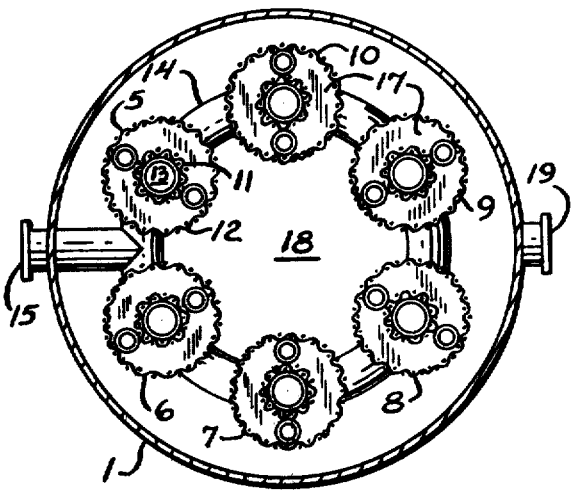
FIG. 2
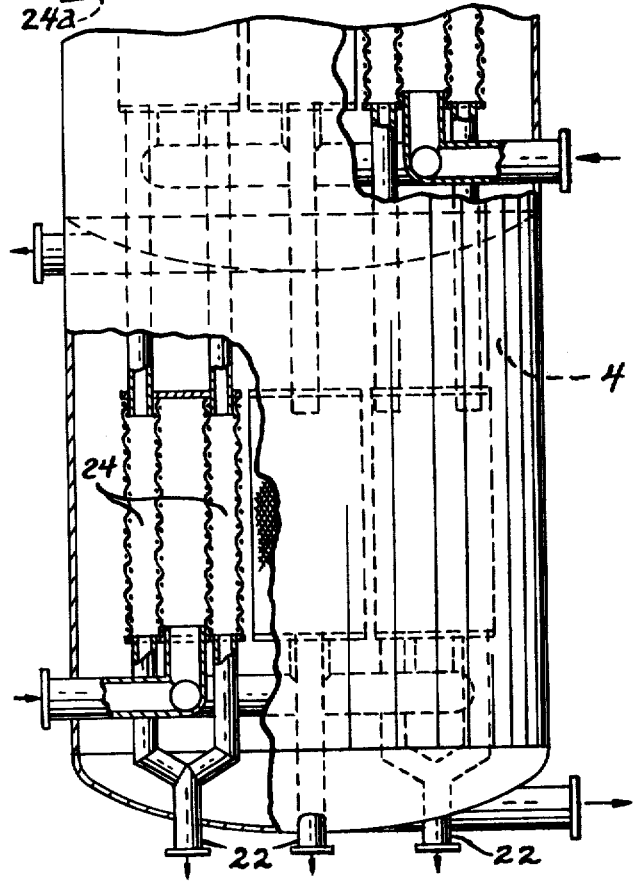

MULTIPLE STAGE REACTOR SYSTEM

CROSS-REFERENCE TO RELATED APPLICATION

This application is a continuation-in-part of our prior copending application Ser. No. 334,502 filed on Dec. 28, 1981. The entire teaching of our prior application is hereby incorporated by reference.

BACKGROUND OF THE INVENTION

The present invention relates to a multiple stage reactor system which is particularly useful in the vapor phase conversion of various hydrocarbon feedstocks. The reactor system provides for the processing of a reactant stream through two or more vertically spaced reaction chambers, said reactant stream being processed in radial flow contact with catalyst particles that are movable through said reaction chambers as a plurality of annular-form beds via gravity flow.

Various vapor phase conversion processes have heretofore been effected utilizing a reactor system wherein a reactant stream is processed in radial flow through a vertically positioned annular-form catalyst bed—an arrangement that offers many design and operating advantages, particularly with respect to those vapor phase processes for the conversion of hydrocarbons. Illustrative of a reactor system wherein a reactant stream is caused to flow laterally and radially through an annular-form catalyst bed is that described in U.S. Pat. No. 2,683,654. The reactor system illustrated is intended for a fixed bed operation. A reactant stream charged to a reaction chamber flows from an outer annular-form space created between the chamber walls and the annular-form catalyst bed, said stream flowing laterally and radially through said catalyst bed and into a perforated centerpipe to be discharged from the reaction chamber. U.S. Pat. No. 3,692,496 describes a somewhat related reactor system in that a reactant stream charged to a reaction chamber is caused to flow laterally and radially from an outer annular-form space through an annular-form catalyst section and into an inner or center manifold to be discharged from said chamber. In the latter case, the reactor system comprises stacked reaction chambers (and consequently stacked annular-form catalyst sections) designed to process catalyst particles downwardly via gravity flow from one annular-form catalyst section to the next lower annular-form catalyst section, the catalyst particles being recovered from the lowermost reaction chamber for regeneration. A variation of the last-described reactor system appears in U.S. Pat. No. 3,725,248 wherein the annular-form catalyst sections are individually contained in side-by-side reaction chambers and in U.S. Pat. No. 3,882,015 wherein the reactant stream is reversed to flow laterally and radially from a center reactant conduit through an annular-form catalyst section and into an outer annular-form space formed by the annular-form catalyst section and the reaction chamber walls.

In addition to the foregoing reactor systems in which the reactant stream is processed laterally and radially across an annular-form catalyst bed, reactor systems comprising multiple catalyst beds in a single reactor vessel have been utilized. For example, U.S. Pat. No. 4,040,794 discloses a reactor wherein the reactants flow laterally and radially across an annular-form moving catalyst bed. However, this reactor system also employs baffles attached along the sides of the annular-form catalyst bed to channel reactant flow in such a manner as to create several distinct serially connected catalyst beds from a single bed of catalyst within one reactor vessel. U.S. Pat. No. 2,617,718 discloses a further reactor system of the stationary type comprising a reactor housing with a plurality of catalyst containers located therein. The catalyst containers are depicted an annular-form catalyst beds emplaced within foraminous containers. The inlet and outlet baffles as well as the emplacement of the catalyst containers act to channel reactant flow in such a manner as to create a plurality of catalyst beds in parallel arrangement. In addition, there are baffles situated around and within each catalyst container to promote uniform flow of reactants across the annular-form catalyst beds.

The foregoing reactor systems have heretofore been described with respect to vapor phase conversion processes wherein they are employed to effect a number of catalyst-promoted conversions. Prominent among such conversion processes are the hydrocarbon conversion processes and include catalytic reforming, hydrogenation, hydrocracking, hydrorefining, isomerization and dehydrogenation, as well as alkylation, transalkylation, steam reforming and the like. The reactor system of the present invention can be similarly employed, but is of particular advantage with respect to a relatively low pressure operation, such as propane and/or butane dehydrogenation at near atmospheric pressures.

BRIEF SUMMARY OF THE INVENTION

The reactor system of the present invention provides for at least two vertically spaced or stacked reaction chambers, each of which contains a plurality of annular-form catalyst-retaining sections for the containment of catalyst particles whereby a reactant stream is distributed amongst said plurality to effect a minimal pressure drop—a feature which is of particular advantage with respect to a relatively low pressure hydrocarbon conversion process. Briefly, the reactor system of this invention comprises two or more vertically spaced or stacked reaction chambers each of which contains two or more vertically positioned annular-form catalyst-retaining sections existing side-by-side, each of said catalyst-retaining sections being defined by an inner tubular-form catalyst-retaining screen (typically supported by a perforated or slotted centerpipe) coaxially disposed within a vertically positioned outer tubular-form catalyst-retaining screen. Catalyst particles are movable through the resulting annular-form catalyst sections in a dense phase via gravity flow. A reactant stream is processed serially through said reaction chambers. In each reaction chamber, the reactant stream may be distributed into each of said annular-form catalyst-retaining sections by way of a fluid flow conduit created by the inner catalyst-retaining screen, the reactant stream being directed outwardly from said conduit, through the annular-form catalyst-retaining section in a substantially radial flow, and into the void space of the reaction chamber to be recovered in admixture with the effluent from the other annular-form catalyst-retaining sections contained therein. Alternatively, the reactant stream may be introduced into the reaction chamber void space and distributed into each of said annular-form catalyst-retaining sections across the outer catalyst-retaining screen, the reactant stream being in each case directed inwardly from said outer catalyst screen, through the annular-form catalyst-retaining section in a substantially radial flow, and into the fluid flow conduit defined by the inner catalyst-retaining screen to be recovered in admixture with the effluent from the other reaction chamber annular-form catalyst-retaining sections by way of a manifold. Additionally the reaction chamber of the present invention has associated therewith first and second ports both located in one of said extremities. The first and second ports serve as means for introducing reactants to the reaction chamber and as means for withdrawing the reaction effluents. It should be noted that, in contrast to the reactor system of the present invention, the reactor systems previously described do not employ a plurality of catalyst-retaining sections in a single reaction chamber in conjunction with the advantageous location of the reactant and reaction effluent ports.

DETAILED DESCRIPTION OF THE INVENTION

In one of its broad aspects, the present invention embodies a multiple stage reactor system which comprises, in combination, a vertically elongated confined reactor vessel; at least two vertically spaced reaction chambers within said vessel, each having upper and lower extremities; a first port and a second port associated with each chamber, both located in one of said extremities; each of said chambers containing a plurality of side-by-side annular-form vertically aligned catalyst-retaining sections positioned therein; each of said catalyst-retaining sections being defined by an inner tubular-form catalyst-retaining screen coaxially disposed within an outer vertically positioned tubular-form catalyst-retaining screen, said inner catalyst-retaining screen further defining a fluid flow conduit within the inner space thereof; each of said chambers containing a first flow manifold connecting said first port to one extremity of each of said fluid flow conduits; each of said catalyst-retaining sections being further defined by two transverse partitions, one connected to the upper extremity of said fluid flow conduit and to the upper perimeter of said outer catalyst-retaining screen, and the other connected to the lower extremity of said fluid flow conduit and to the lower perimeter of said outer catalyst-retaining screen; each of said chambers having a void space in open communication with said second port, and defined by the inner walls of said chamber and the outer surface of the plurality of catalyst-retaining sections contained therein, said void space serving as a second flow manifold connecting the outer surface of said plurality of catalyst-retaining sections to said second port; catalyst inlet conduits extending through the upper extremity of the uppermost chamber and connected in open communication with the upper extremity of each of the catalyst-retaining sections contained therein; inter-chamber catalyst conduits connecting the lower extremity of each catalyst-retaining section in each reaction chamber, except the catalyst-retaining sections in the lowermost chamber, in open communication with the upper extremity of a catalyst-retaining section in the next lower chamber; and catalyst withdrawal conduits connected in open communication with the lower extremity of each of the catalyst-retaining sections contained in the lowermost chamber and extending through the lower extremity thereof, whereby catalyst particles are gravitated through said vertically spaced reaction chambers via the plurality of catalyst-retaining sections contained therein.

One of the more specific embodiments concerns a multiple stage reactor system which comprises, in combination, a vertically elongated confined reactor vessel; three vertically spaced reaction chambers within said vessel each having upper and lower extremities; a first port and a second port associated with each chamber, both located in the lower extremity thereof; each of said chambers containing six side-by-side vertically aligned annular-form catalyst-retaining sections circumferentially spaced therein; each of said catalyst-retaining sections being defined by an inner tubular-form catalyst-retaining screen coaxially disposed within an outer vertically positioned tubular-form catalyst-retaining screen, said inner catalyst-retaining screen further defining a fluid flow conduit within the inner space thereof; each of said chambers containing a first flow manifold connecting the first port to the lower extremity of each of the fluid flow conduits contained therein; each of said catalyst-retaining sections being further defined by two transverse partitions, one connected to the upper extremity of said fluid flow conduit and to the upper perimeter of said outer catalyst-retaining screen and the other connected to the lower extremity of said fluid flow conduit and to the lower perimeter of said outer catalyst-retaining screen; each of said chambers having a void space in open communication with the second port and defined by the inner walls of the chamber and the outer surface of said catalyst-retaining sections contained therein, said void space serving as a second flow manifold connecting the outer surface of said catalyst-retaining sections to said second port; catalyst inlet conduits extending through the upper extremity of the uppermost chamber and connected in open communication with each of the catalyst-retaining sections contained therein; inter-chamber catalyst conduits connecting the lower extremity of each catalyst-retaining section in each reaction chamber, except the lowermost chamber, in open communication with the upper extremity of a catalyst-retaining section in the next lower chamber; and catalyst withdrawal conduits connected in open communication with the lower extremity of each of the catalyst-retaining sections contained in the lowermost chamber and extending through the lower extremity thereof, whereby catalyst particles are gravitated through said vertically spaced reaction chambers via the plurality of catalyst-retaining sections contained therein.

In another aspect, the invention broadly embodies a process for the conversion of a hydrocarbon charge stock characterized in that the hydrocarbon charge stock is passed in vapor phase to a multiple stage reactor system comprising, in combination, a vertically elongated confined reactor vessel; at least two vertically spaced reaction chambers within said vessel, each having upper and lower extremities; a first port and a second port associated with each chamber, both located in one of said extremities; each of said chambers containing a plurality of side-by-side annular-form vertically aligned catalyst-retaining sections positioned therein; each of said catalyst-retaining sections being defined by an inner tubular-form catalyst-retaining screen coaxially disposed within an outer vertically positioned tubular-form catalyst-retaining screen, said inner catalyst-retaining screen further defining a fluid flow conduit within the inner space thereof; each of said chambers containing a first flow manifold connecting said first port to one extremity of each of said fluid flow conduits; each of said catalyst-retaining sections being further defined by two transverse partitions, one connected to the upper extremity of said fluid flow conduit and to the upper perimeter of said outer catalyst-retaining screen, and the other connected to the lower extremity of said fluid flow conduit and to the lower perimeter of said outer catalyst-retaining screen; each of said chambers having a void space in open communication with said second port, and defined by the inner walls of said chamber and the outer surface of the plurality of catalyst-retaining sections contained therein, said void space serving as a second flow manifold connecting the outer surface of said plurality of catalyst-retaining sections to said second port; catalyst inlet conduits extending through the upper extremity of the uppermost chamber and connected in open communication with the upper extremity of each of the catalyst-retaining sections contained therein; inter-chamber catalyst conduits connecting the lower extremity of each catalyst-retaining section in each reaction chamber, except the catalyst-retaining sections in the lowermost chamber, in open communication with the upper extremity of a catalyst-retaining section in the next lower chamber; and catalyst withdrawal conduits connected in open communication with the lower extremity of each of the catalyst-retaining sections contained in the lowermost chamber and extending through the lower extremity thereof, whereby catalyst particles are gravitated through said vertically spaced reaction chambers via the plurality of catalyst-retaining sections contained therein.

In a further embodiment of the process of the invention, the hydrocarbon feedstock is subjected to catalytic dehydrogenation in the multiple stage reactor system in the presence of a dehydrogenation catalyst emplaced within the catalyst-retaining sections.

The further description of the reactor system of the present invention is presented with reference to the attached schematic drawing.

FIG. 1 of the drawing represents a side view of a reactor system in accordance with the present invention which is partially broken away and sectioned.

FIG. 2 is a sectional view of the reactor system looking down from the upper reaction chamber.

The drawing is presented in illustration of one preferred embodiment of the invention and is not intended as an undue limitation on the generally broad scope of the invention as set out in the appended claims. While each reaction chamber is depicted as comprising a first flow manifold connecting a first port to the lower extremity of each of a plurality of fluid flow conduits, as well as a second port at the lower extremity of each reaction chamber, it is understood that said flow manifold may be connected to the upper extremity of each of said fluid flow conduits and to the first port with said first and second ports being then located in the upper extremity of each of the reaction chambers.

Additionally, even though reactant flow across each catalyst-retaining section is depicted as being from the fluid flow conduit radially outward toward the outer catalyst-retaining screen, the flow pattern through the reactor system may be advantageously reversed depending on the specific application. Hence reactant flow across the catalyst-retaining sections may be radially inward from the outer catalyst-retaining screen toward the fluid flow conduit.

Moreover, in the multiple stage or multiple reaction chamber system, fresh and/or regenerated catalyst particles may be added continuously or intermittently to an initial or top reaction chamber and processed serially or sequentially through the reactor system, said particles being withdrawn from the final or bottom reaction chamber, as the case may be, for subsequent regeneration. In the preferred reactor system comprising stacked reaction chambers, the reactor system will in effect comprise a plurality of annular-form catalyst beds, each of which is movable downwardly from the top reaction chamber and through the reactor system as a substantially unbroken or continuous annular-form column to be recovered from the bottom reaction chamber. Thus, all reaction chambers are maintained on-stream while fresh and/or regenerated catalyst particles are added to the top reaction chamber, and used catalyst particles are recovered from the bottom reaction chamber to effect a substantially continuous process.

Referring then to the drawing, there is shown a vertically elongated confined reactor vessel 1 having three vertically spaced confined reaction chambers 2, 3 and 4. Each of said reaction chambers is further shown as containing six annular-form catalyst-retaining sections in vertical alignment with those of the vertically adjacent reaction chamber or chambers. All of said catalyst-retaining sections being substantially identical, the description of those contained in the uppermost reaction chamber 2 will serve to also describe those contained in the intermediate reaction chamber 3 and in the lowermost reaction chamber 4. Thus, all of the catalyst-retaining sections 5, 6, 7, 8, 9 and 10 contained in reaction chamber 2 are visible in the sectional top view, FIG. 2. Catalyst-retaining sections 5, 7 and 8 are visible in a sectional plan view, FIG. 1, with catalyst-retaining section 6 and those sections in chambers 3 and 4 in vertical alignment therewith being not shown to provide a more complete view of first flow manifold 14. The catalyst-retaining sections are preferably circumferentially spaced as illustrated since this arrangement permits ready access to each of said sections for repair or replacement should the need arise. In any case, from four to about seven catalyst-retaining sections are preferred per reaction chamber.

All of said annular-form catalyst-retaining sections, as exemplified by catalyst-retaining section 5, comprise an inner tubular-form catalyst retaining screen 11 coaxially disposed within a vertically positioned outer tubular-form catalyst-retaining screen 12. The inner tubular-form catalyst-retaining screen 11 further defines a fluid flow conduit 13 within the inner space thereof. A first flow manifold 14 is connected to the lower extremity of each of the fluid flow conduits whereby a reactant stream introduced into a reaction chamber, e.g., reaction chamber 2, by way of an inlet port, e.g., first port 15, is distributed into each of said fluid flow conduits. Transverse partition 16 is connected to the upper extremity of fluid flow conduit 13 and to the upper perimeter of outer catalyst-retaining screen 12 while transverse partition 17 is connected to the lower extremity of fluid flow conduit 13 and to the lower extremity of outer catalyst-retaining screen 12. A reactant stream rising through fluid flow conduit 13 is thereby directed laterally and radially outward through annular-form catalyst-retaining section 5 and into void space 18 where the effluent from the plurality of catalyst-retaining section is collected to be discharged through second port 19 which is in open communication with void space 18. The void space 18 is defined by the interior walls of the reaction chamber, e.g., reaction chamber 2, and the outer surface of the catalyst-retaining sections therein, e.g., catalyst-retaining sections 5, 6, 7, 8, 9 and 10.

The flow as described above is such that the reactants flow radially outward from fluid flow conduit 13 across the catalyst bed to void space 18. As noted earlier, the flow pattern through the reactor system alternatively may be such that the reactant stream enters via second port 19 into void space 18 thereby flowing laterally and radially inward across the catalyst bed and into fluid flow conduit 13 for withdrawal via first flow manifold 14 and first port 15. Thus first port 15 may act as an inlet or outlet port and second port 19 will correspondingly act as an outlet or inlet port.

Catalyst inlet conduit 20, catalyst transfer conduit 21 and catalyst withdrawal conduit 22 provide for the gravity flow of catalyst particles through the vertically stacked reaction chambers via the plurality of catalyst-retaining sections contained therein. As noted above, each of said catalyst-retaining sections contain a lower transverse partition 17 extending between the lower extremity of the fluid flow conduit 13 and the lower perimeter of outer catalyst-retaining screen 12 whereby catalyst particles descending through said catalyst-retaining sections are directed through said catalyst conduits. Using catalyst-retaining section 5 and catalyst-retaining sections 24A and 24 in vertical alignment therewith as an example, fresh and/or regenerated catalyst particles are introduced through the uppermost extremity of the uppermost reaction chamber 2 by way of catalyst inlet conduit 20. Th catalyst inlet conduit is shown as connected in open communication with catalyst-retaining section 5 by way of two outlets. However, said outlets may be but two of a multiple of outlets circumferentially spaced about the annular-form catalyst-retaining section to ensure a uniform distribution of catalyst particles therein. Inter-chamber catalyst transfer conduit 21 is simlarly spaced to provide a substantially uniform gravitational flow of catalyst particles from the uppermost catalyst-retaining section 5 to the next lower catalyst-retaining section 24A in vertical alignment therewith, and from the last mentioned catalyst-retaining section to the vertically aligned lowermost catalyst-retaining section 24. Catalyst particles are withdrawn from the annular-form catalyst-retaining section 24 by way of catalyst withdrawal conduit 22. The conduits are shown as connected in open communication with the catalyst-retaining section 24 by way of two outlets. These again may be but two of a multiple of withdrawal outlets, generally from about four to about eight, circumferentially spaced about the lower extremity of the lowermost catalyst-retaining section 24. The gravity flow of catalyst particles through the vertically stacked reaction chambers via the remaining vertically aligned annular-form catalyst-retaining sections is effected substantially as described with respect to the vertically aligned annular-form catalyst-retaining sections 5, 24A and 24.

In the embodiment depicted in the drawing, first port 15 and second port 19 are shown to be situated in the lower extremity of reaction chamber 2 and first flow manifold 14 correspondingly connects first port 15 to the lower extremity of fluid flow conduit 13. Alternatively, both ports may be situated in the upper extremity of the reaction chamber. When both ports are so located, first flow manifold 14 will then correspondingly connect first port 15 to the upper extremity of the fluid flow conduits. By connecting first flow manifold 14 to the extremity of the fluid flow conduits which correspond to the reaction chamber extremity in which first port 15 and second port 19 are located, two major advantages result. First, the amount of internal conduit comprising the first flow manifold is minimized thereby resulting in reduced cost and lower pressure drop through the reaction chamber. Second, the velocity heads of the vapor in the fluid flow conduits and in the void space surrounding the catalyst-retaining sections become balanced thereby promoting a more uniform flow of vapor across the length of the catalyst-retaining sections. The upper velocity heads become balanced as a result of the vapor flow path through the fluid flow conduits and through the reaction chamber void space. The velocity head of the vapor decreases as the vapor passes along the length of the fluid flow conduit. Accordingly then, the vapor velocity head is at a maximum at the inlet to the fluid flow conduit and is essentially zero at the terminal end (the upper end in FIG. 1) thereof. As the velocity head of the vapor decreases, the pressure of the vapor increases. Therefore, the vapor pressure at the fluid flow conduit inlet is less than the vapor pressure at the terminal end of the fluid flow conduit and there accordingly exists a vapor pressure gradient along the fluid flow conduit from the inlet to the terminal end thereof. In order to assure uniform flow of vapor across the catalyst beds contained in the annular catalyst-retaining sections, a corresponding vapor pressure gradient must be induced in the void space and therefore, the vapor velocity head in the void space must correspondingly decrease in the same direction as that in the fluid flow conduit to assure a corresponding vapor pressure gradient on the void space side of the catalyst-retaining sections. The vapor flow in the void space must be such that a minimum vapor velocity head therein occurs at a point corresponding to the terminal end of fluid flow conduits and a maximum vapor velocity head therein occurs at a point corresponding to the inlet of the fluid flow conduits. Such a vapor flow will occur in the void space if the flow of vapor therein is in the opposite direction to the flow of vapor in the fluid flow conduit. If, contrary to the above, the vapor flow in the void space is in the same direction as that in the fluid flow conduit, the vapor pressure gradient in the void space will be the opposite of that in the fluid flow conduit and will result in non-uniform flow of vapor across the annular catalyst bed. Accordingly then, the advantages to be derived by situating the first port and the second port in the same extremity of the reaction chamber becomes apparent. By so situating the ports, it is possible to induce vapor flow patterns through the void space and the fluid flow conduits which result in a more uniform flow of vapor across the annular catalyst bed. Moreover, the improvement in the uniformity of vapor flow will be achieved regardless of whether the first port and second port are both located in the upper or lower extremity of the reaction chamber or whether the flow is outward from the fluid flow conduits to the void space or inward from the void space to the fluid flow conduits.

The reactor system of the present invention is of particular advantage with respect to the conversion of hydrocarbons and in particular the dehydrogenation of hydrocarbons in the presence of a dehydrogenation catalyst—an established and well known hydrocarbon conversion process in the petroleum refining industry. The invention offers special advantage when the hydrocarbon charge stock to be dehydrogenated comprises $C_2+$ normally gaseous hydrocarbons with the desired product comprising the corresponding monolefins. The monoolefinic products are generally useful as intermediates in the production of other more valuable products, and the catalytic dehydrogenation process is typically utilized in conjunction with various other hydrocarbon conversion processes to yield a desired final product. For example, utilizing liquid petroleum gas (LPG)—a compressed or liquefied gas consisting of propane and butane or mixed butanes—as a starting material, catalytic dehydrogenation can be utilized to produce propylene and/or butylenes in conjunction with an HF alkylation unit wherein said olefins are alkylated with isobutane to produce a high octane motor fuel; or in conjunction with a catalytic condensation unit wherein said olefins are condensed to form tetramers or polymer gasoline; or in conjunction with an etherification unit wherein isobutylene is reacted with methanol to produce methyl t-butyl ether, a highly desirable gasoline additive.

The catalytic dehydrogenation process will preferably utilize a catalytic composite comprising a platinum group metal component, a tin component, and an alkali metal component composited with a porous, high surface area, adsorbent support or carrier material. Of the platinum group metals, i.e., platinum, palladium, ruthenium, rhodium, osmium and iridium, platinum is a preferred catalyst component. The platinum component will generally comprise from about 0.01 to about 2.0 wt.% of the catalytic composite, and the tin component will generally comprise from about 0.01 to about 5 wt.% thereof. Of the alkali metals, i.e., cesium, rubidium, potassium, sodium and lithium, lithium and/or potassium are preferred. The alkali metal will generally constitute from about 0.1 to about 3.5 wt.% of the catalytic composite. One preferred catalytic composite comprises from about 0.1 to about 1.0 wt.% platinum, and from about 0.1 to about 1.0 wt.% tin and from about 0.2 to about 3.0 wt.% lithium or potassium composited with a porous adsorbent support or carrier material having a surface area of from about 25 to about 500 m$^2$/g. The preferred carrier materials are the refractory inorganic oxides with best results being obtained with an alumina support or carrier material.

The catalytic dehydrogenation process herein contemplated is a relatively high temperature operation effected at a temperature of from about 900° to about 1300° F., and preferably from about 1000° to about 1250° F. The process is also a relatively low pressure operation effected at a pressure of from about 0 to about 35 psig, preferably from about 10 to about 30 psig. The reactor system of this invention is of still further advantage with respect to the relatively high temperature operation in that the flow pattern may be such that the reactants have minimal exposure to thermal conversion conditions prior to contact with the dehydrogenation catalyst to substantially obviate conversion to other than the desired dehydrogenation products. This is accomplished by distributing the inlet reactant stream directly into each of the fluid flow conduits formed by the inner catalyst-retaining screens thereby creating a reactant flow path outward from the fluid flow conduits. In this manner, the reactant stream is exposed to the high inlet temperature for a relatively brief period while it passes through the first flow manifold and the fluid flow conduits. While the residence time of the reactant stream in the relatively high capacity void space outside of the annular-form catalyst beds is substantially longer, thermal conversion is negligible because of the drop in reactant stream temperature resulting from the endothermic nature of the dehydrogenation reaction.

The reactor system of this invention is of particular advantage with respect to the relatively low pressure operation in that it allows a high throughput with minimal pressure drop. This results from the multiple annular-form catalyst-retaining sections employed herein as opposed to the more conventional unitary annular-form catalyst-retaining sections. Generally from four to seven catalyst-retaining sections per reaction chamber in the process of the invention with six being preferred. Each catalyst-retaining section provides an overall annular-form catalyst bed having a larger cross-sectional area allowing for a relatively shallow catalyst bed. The radially flowing reactant stream thus experiences a minimal pressure drop across the bed. In addition, the relatively low pressure drop facilitates the gravitational flow of catalyst particles through the multiple annular-form catalyst-retaining sections.

Notwithstanding that the catalytic dehydrogenation process involves hydrogen-producing reactions, it has been the practice to charge hydrogen to the reaction zone, typically recycle hydrogen, in admixture with the hydrocarbon feedstock—a practice which has been found to promote catalyst activity as well as activity-stability. Dehydrogenation conditions thus further include a hydrogen to hydrocarbon mole ratio of from about 1 to about 10, and more suitably from about 1 to about 4. The hydrocarbon reactant stream is also suitably charged at a rate to provide a liquid hourly space velocity of from about 2 to about 6.

Thus, in the preferred catalytic dehydrogenation process herein contemplated, a hydrogen/hydrocarbon reactant stream is preheated to provide desired temperature conditions in the uppermost reaction chamber 2. The reactant stream is introduced into said reaction chamber by way of first port 15 and distributed to each of the annular-form catalyst-retaining sections 5, 6, 7, 8, 9 and 10 by means of first flow manifold 14 and by way of the fluid flow conduit 13. The reactant stream then passes radially and laterally through each of the annular-form catalyst-retaining sections in contact with the gravitating catalyst bed and is collected in void space 18. The reactant stream is recovered through second port 19, reheated in an external heating means, not shown, and recharged to the next lower reaction chamber 3. The reactant stream is processed through reaction chamber 3 substantially as described with respect to reaction chamber 2, the reactant stream being withdrawn from chamber 3, reheated in a heating means, not shown, and recharged to the lowermost reaction chamber 4 wherein it is similarly processed. The reactant stream is recovered from the lowermost reaction chamber 4 for further processing.

We claim as our invention:

1. A multiple stage reactor system which comprises, in combination:
   (a) a vertically elongated confined reactor vessel;
   (b) at least two vertically spaced reaction chambers within said vessel, each having upper and lower extremities;
   (c) a first port and a second port associated with each chamber, both located in one of said extremities;
   (d) each of said chambers containing a plurality of side-by-side annular-form vertically aligned catalyst-retaining sections positioned therein;

(e) each of said catalyst-retaining sections being defined by an inner tubular-form catalyst-retaining screen coaxially disposed within an outer vertically positioned tubular-form catalyst-retaining screen, said inner catalyst-retaining screen further defining a fluid flow conduit within the inner space thereof;

(f) each of said chambers containing a first flow manifold connecting said first port to one extremity of each of said fluid flow conduits;

(g) each of said catalyst-retaining sections being further defined by two transverse partitions, one connected to the upper extremity of said fluid flow conduit and to the upper perimeter of said outer catalyst-retaining screen, and the other connected to the lower extremity of said fluid flow conduit and to the lower perimeter of said outer catalyst-retaining screen;

(h) each of said chambers having a void space in open communication with said second port, and defined by the inner walls of said chamber and the outer surfaces of the plurality of catalyst-retaining sections contained therein, said void space serving as a second flow manifold connecting the outer surface of said plurality of catalyst-retaining sections to said second port;

(i) catalyst inlet conduits extending through the upper extremity of the uppermost chamber and connected in open communication with the upper extremity of each of the catalyst-retaining sections contained therein;

(j) inter-chamber catalyst conduits connecting the lower extremity of each catalyst-retaining section in each reaction chamber, except the catalyst-retaining sections in the lowermost chamber, in open communication with the upper extremity of a catalyst-retaining section in the next lower chamber; and, (k) catalyst withdrawal conduits connected in open communication with the lower extremity of each of the catalyst-retaining sections contained in the lowermost chamber and extending through the lower extremity thereof, whereby catalyst particles are gravitated through said vertically spaced reaction chambers via the plurality of catalyst-retaining sections contained therein.

2. The reactor system of claim 1 further characterized in that each of said reaction chambers contains from four to seven of said side-by-side annular form catalyst-retaining sections.

3. The reactor system of caim 2 further characterized in that each of said reaction chambers contains six of said side-by-side catalyst-retaining sections circumferentially spaced therein.

4. The reactor system of claim 1 further characterized in that said first flow manifold in each chamber connects the first port of the chamber with a lower extremity of each of said fluid flow conduits within the chamber.

5. The reactor system of claim 4 further characterized in that said first and second ports of each chamber are located at the lower extremity thereof.

6. The reactor system of claim 1 further characterized in that said first flow manifold in each chamber connects the first part of the chamber with an upper extremity of each of said fluid flow conduits within the chamber.

7. The reactor system of claim 5 further characterized in that said first and second ports of each chamber are located at the upper extremity thereof.

8. The reactor system of claim 1 further characterized in that said first port of each chamber is a reactant inlet port and said second port of each chamber is a reaction effluent outlet port.

9. The reactor system of claim 1 further characterized in that said first port of each chamber is a reaction effluent outlet port and said second port of each chamber is a reactant inlet port.

10. A process for the conversion of a hydrocarbon charge stock characterized in that the hydrocarbon charge stock is passed in vapor phase to a multiple stage reactor system comprising, in combination:

(a) a vertically elongated confined reactor vessel;

(b) at least two vertically spaced reaction chambers within said vessel, each having upper and lower extremities;

(c) a first port and a second port associated with each chamber, both located in one of said extremities;

(d) each of said chambers containing a plurality of side-by-side annular-form vertically aligned catalyst-retaining sections positioned therein;

(e) each of said catalyst-retaining sections being defined by an inner tubular-form catalyst-retaining screen coaxially disposed within an outer vertically positioned tubular-form catalyst-retaining screen, said inner catalyst-retaining screen further defining a fluid flow conduit within the inner space thereof;

(f) each of said chambers containing a first flow manifold connecting said first port to one extremity of each of said fluid flow conduits;

(g) each of said catalyst-retaining sections being further defined by two transverse partitions, one connected to the upper extremity of said fluid flow conduit and to the upper perimeter of said outer catalyst-retaining screen, and the other connected to the lower extremity of said fluid flow conduit and to the lower perimeter of said outer catalyst-retaining screen;

(h) each of said chambers having a void space in open communication with said second port, and defined by the inner walls of said chamber and the outer surface of the plurality of catalyst-retaining sections contained therein, said void space serving as a second flow manifold connecting the outer surface of said plurality of catalyst-retaining sections to said second port;

(i) catalyst inlet conduits extending through the upper extremity of the uppermost chamber and connected in open communication with the upper extremity of each of the catalyst-retaining sections contained therein;

(j) inter-chamber catalyst conduits connecting the lower extremity of each catalyst-retaining section in each reaction chamber, except the catalyst-retaining sections in the lowermost chamber, in open communication with the upper extremity of a catalyst-retaining section in the next lower chamber; and, (k) catalyst withdrawal conduits connected in open communication with the lower extremity of each of the catalyst-retaining sections contained in the lowermost chamber and extending through the lower extremity thereof, whereby catalyst particles are gravitated through said vertically spaced reaction chambers via the plurality of catalyst-retaining sections contained therein.

11. The process of claim 10 further characterized in that said hydrocarbon feedstock is subjected to catalytic dehydrogenation in the reactor system in the presence of a dehydrogenation catalyst emplaced within the catalyst-retaining sections.

12. The process of claim 11 further characterized in that said hydrocarbon charge stock comprises $C_2+$ normally gaseous hydrocarbons.

13. The process of claim 12 further characterized in that the hydrocarbon charge stock comprises propane or butane.

14. The process of claim 10 further characterized in that said first flow manifold in each chamber connects the first port with a lower extremity of each of said fluid flow conduits within the chamber.

15. The process of claim 10 further characterized in that each of said reaction chambers contains from four to seven of said side-by-side annular-form vertically aligned catalyst-retaining sections.

16. The process of claim 15 further characterized in that each of said reaction chambers contains six of said side-by-side annular-form vertically aligned catalyst-retaining sections circumferentially spaced therein.

17. The process of claim 10 further characterized in that said first and second ports are located at the lower extremity of said reaction chamber.

18. The process of claim 10 further characterized in that said first port of each chamber is a hydrocarbon charge stock inlet port and said second port of each chamber is a reaction effluent outlet port.

19. The process of claim 10 further characterized in that said second port is a hydrocarbon charge stock inlet port and said first port is a reaction effluent outlet port.

20. The process of claim 10 further characterized in that said first and second ports of each chamber are located at the upper extremity thereof.

* * * * *